US009024048B2

(12) United States Patent
Kapellen et al.

(10) Patent No.: US 9,024,048 B2
(45) Date of Patent: May 5, 2015

(54) APPARATUS AND METHODS TO PRESERVE CATALYST ACTIVITY IN AN EPOXIDATION PROCESS

(75) Inventors: Mark Kapellen, Vondelingenplaat (NL); Bart Van Den Berg, Vondelingenplaat (NL); Prasad Muppa, Vondelingenplaat (NL); Paul Haesakkers, Vondelingenplaat (NL)

(73) Assignee: Evonik Degussa GmbH, Rellinghauser Strasse, Essen (DE)

( * ) Notice: Subject to any disclaimer, the term of this patent is extended or adjusted under 35 U.S.C. 154(b) by 0 days.

(21) Appl. No.: 14/124,989

(22) PCT Filed: Jun. 13, 2012

(86) PCT No.: PCT/EP2012/002527
§ 371 (c)(1), (2), (4) Date: Dec. 18, 2013

(87) PCT Pub. No.: WO2012/175182
PCT Pub. Date: Dec. 27, 2012

(65) Prior Publication Data

US 2014/0113801 A1 Apr. 24, 2014

(30) Foreign Application Priority Data

Jun. 22, 2011 (EP) .................................... 11005091

(51) Int. Cl.
*C07D 301/06* (2006.01)
*C07D 301/12* (2006.01)
*B01J 31/40* (2006.01)

(52) U.S. Cl.
CPC ........... *B01J 31/4092* (2013.01); *C07D 301/12* (2013.01)

(58) Field of Classification Search
CPC . C07D 301/12; C07D 301/06; B01J 31/4092; B01J 31/40
USPC ............................................ 549/531; 502/25
See application file for complete search history.

(56) References Cited

U.S. PATENT DOCUMENTS

| | | | | |
|---|---|---|---|---|
| 4,973,718 A | | 11/1990 | Buchler et al. | |
| 5,153,161 A | | 10/1992 | Kerschner et al. | |
| 5,155,274 A | | 10/1992 | Herrmann et al. | |
| 5,274,147 A | | 12/1993 | Kerschner et al. | |
| 5,329,024 A | | 7/1994 | Jureller et al. | |
| 5,429,769 A | | 7/1995 | Nicholson et al. | |
| 5,516,738 A | * | 5/1996 | Jureller et al. | 502/155 |
| 5,833,755 A | | 11/1998 | Schlom et al. | |
| 6,087,513 A | | 7/2000 | Liao et al. | |
| 6,673,950 B1 | * | 1/2004 | Teles et al. | 549/529 |
| 8,729,282 B2 | * | 5/2014 | Postma et al. | 549/531 |
| 2001/0025695 A1 | | 10/2001 | Patt et al. | |
| 2002/0010120 A1 | | 1/2002 | Hage et al. | |
| 2006/0041150 A1 | | 2/2006 | Catinat et al. | |
| 2010/0029848 A1 | | 2/2010 | Forlin et al. | |

FOREIGN PATENT DOCUMENTS

| | | | |
|---|---|---|---|
| DE | 19923121 | | 11/2000 |
| EP | 0458397 | A2 | 5/1991 |
| EP | 0458398 | A2 | 5/1991 |
| EP | 2149569 | A1 | 2/2010 |
| EP | 2149570 | A1 | 2/2010 |
| JP | 2002145872 | | 5/2002 |
| WO | WO 2004/048353 | A1 | 6/2004 |

OTHER PUBLICATIONS

Murphy et al , Ligand and pH Influence on Manganese Mediated Peracetic acid Expoxidation of Terminal Olefins, 2004, Organic Letters, vol. 6 , No. 18, p. 3119-3122.*

De Vos D E et al., Epoxidation of Terminal or Electron-deficient Olefins with H202, catalysed by Mn-trimethyltriazacyclonane Complexes in the Presence of an Oxalate Buffer, Tetrahedron Letters, vol. 39, No. 2 (May 14, 1998) 3221-3224.

J.W. De Boer, University of Groningen, Doctoral disertation (2008).

T.H. Bennur et al., Journal of Molecular Catalysis. A, Chemical, 185 (2002) 71-80.

A Grenz et al., Chemical Communication (2001) 1726-1727.

Mbeleck et al., Reactive & Functional Polymers, 67 (2007) 1448-1457.

Venturello et al., Journal of Organic Chemisty, vol. 48, No. 21 (1983) 3831-3833.

Sibbons et al., Dalton Transactions (2006) 645-661.

Arends et al. Topics in Catalysis, vol. 19, No. 1 (2002) 133-141.

J.W. De Boer et al., Dalton Transactions (2008) 6283-6295.

Alsters et al., Mechanisms in Homogeneous and Heterogeneous Epoxidation Catalysis, Elsevier Science & Technology (2008) 416-428.

Sherrington et al., Journal of Catalysis, vol. 131, (1991) 115-126.

A.M. D'A Rocha Gonsalves et al., Journal of Molecular Catalysis A: Chemical, vol. 168 (2001) 25-32.

* cited by examiner

*Primary Examiner* — T. Victor Oh
(74) *Attorney, Agent, or Firm* — Linda S. Li; James S. Ngui

(57) ABSTRACT

Apparatus and methods are provided for forming and processing multiphasic systems. In one embodiment, the invention provides a process for the manufacture of an epoxide, including reacting an olefinically unsaturated compound with an oxidant in the presence of a buffer component and a water-soluble manganese complex disposed in an aqueous phase having a first pH level in a first multiphasic system, adjusting the pH of the aqueous phase to a second pH level less than the first pH level, isolating at least a portion of the aqueous phase from the first multiphasic system, adjusting the pH of the at least a portion of the aqueous phase to a third pH level greater than the second pH level, and introducing the at least a portion of the aqueous phase into a second multiphasic system.

15 Claims, 3 Drawing Sheets

APPARATUS AND METHODS TO PRESERVE CATALYST ACTIVITY IN AN EPOXIDATION PROCESS

FIELD OF THE INVENTION

The invention relates to the processing of a catalyst in a multiphasic system and to an apparatus for carrying out the processing of the catalyst.

BACKGROUND OF THE INVENTION

A process for the manufacture of a 1,2-epoxide is described in the published European patent application EP 2149569. The publication describes the catalytic oxidation of an olefinically unsaturated compound using a water soluble manganese complex as the oxidation catalyst. The process described is carried out in a multiphasic system, such as a biphasic system, having an organic phase, which may be a liquid or a gaseous phase, and an aqueous phase. The actual reaction is believed to take place in the aqueous phase, and the resulting epoxide product separates from the aqueous phase into the organic phase due to low solubility of, or extraction or stripping by the organic phase. For this reason, the 1,2-epoxide is produced of a desirable turnover number (TON), with a desirable selectivity towards the 1,2-epoxide, while providing an improved ease of isolating the produced 1,2-epoxide.

While the epoxide product is recovered in the organic phase through a phase separation process, it was observed that the manganese complex is retained in the aqueous phase. Unfortunately, attempts to recover and/or recycle the manganese complex have met with limited success as the manganese complex was observed to deactivate during phase separation when the aqueous phase is not intensively mixed with the organic phase.

Therefore, there is a need for a process and apparatus for recovery or recycling of the manganese complex catalyst system.

SUMMARY OF THE INVENTION

Accordingly, the invention provides for processing a manganese complex between epoxidation reactions without a loss or with a minimal loss in catalytic activity by adjusting a phase containing the manganese complex to a pH level that reduces the deactivation of the manganese complex when not used as catalyst in a reaction, and then at a later time, adjusting the pH of the phase containing the pH to epoxide reaction conditions for use as a catalyst.

In one embodiment, the invention provides a method for processing a multiphasic system including reacting an olefinically unsaturated compound with an oxidant in the presence of a buffer component and a water-soluble manganese complex in an aqueous phase having a first pH level in a first multiphasic system, adjusting the pH of the aqueous phase to a second pH level less than the first pH level, isolating at least a portion of the aqueous phase from the first multiphasic system, adjusting the pH of the at least a portion of the aqueous phase to a third pH level greater than the second pH level, and introducing the at least a portion of the aqueous phase into a second multiphasic system.

In one embodiment, the invention provides an apparatus for a method for processing a multiphasic system including a first reactor adapted to process a multiphasic system, wherein the first reactor has a first outlet line, a second reactor adapted to process a multiphasic system, wherein the second reactor has a second outlet line, one or more component tanks independently fluidly coupled to each of the first reactor and the second reactor, a first phase separator disposed between the first reactor and the second reactor, wherein the phase separator comprises an organic phase outlet line and an aqueous phase outlet line and the first phase separator is fluidly coupled to the first outlet line and is fluidly coupled to the second reactor by the aqueous phase outlet line, an acid-containing line fluidly coupled to the first outlet line between the first reactor and the phase separator, the phase separator, or combinations thereof, and a base-containing line coupled to the phase separator outlet line between the phase separator and the second reactor, the second reactor, or combinations thereof.

The apparatus may further include a third reactor adapted to process a multiphasic system, wherein the third reactor has a third outlet line, one or more component tanks independently fluidly coupled to the third reactor, a second phase separator disposed between the second reactor and the third reactor, wherein the phase separator is fluidly coupled to the second outlet line and is fluidly coupled to the third reactor by a second phase separator aqueous phase outlet line, a second acid-containing line fluidly coupled to the second outlet line between the second reactor and the second phase separator, the second phase separator, or combinations thereof, and a second base-containing line coupled to the second phase separator outlet line between the second phase separator and the third reactor, the third reactor, or combinations thereof.

DETAILED DESCRIPTION OF THE FIGURES

The following is a brief description of figures wherein like numbering indicates like elements.

DETAILED DESCRIPTION OF THE INVENTION

Figure 1:
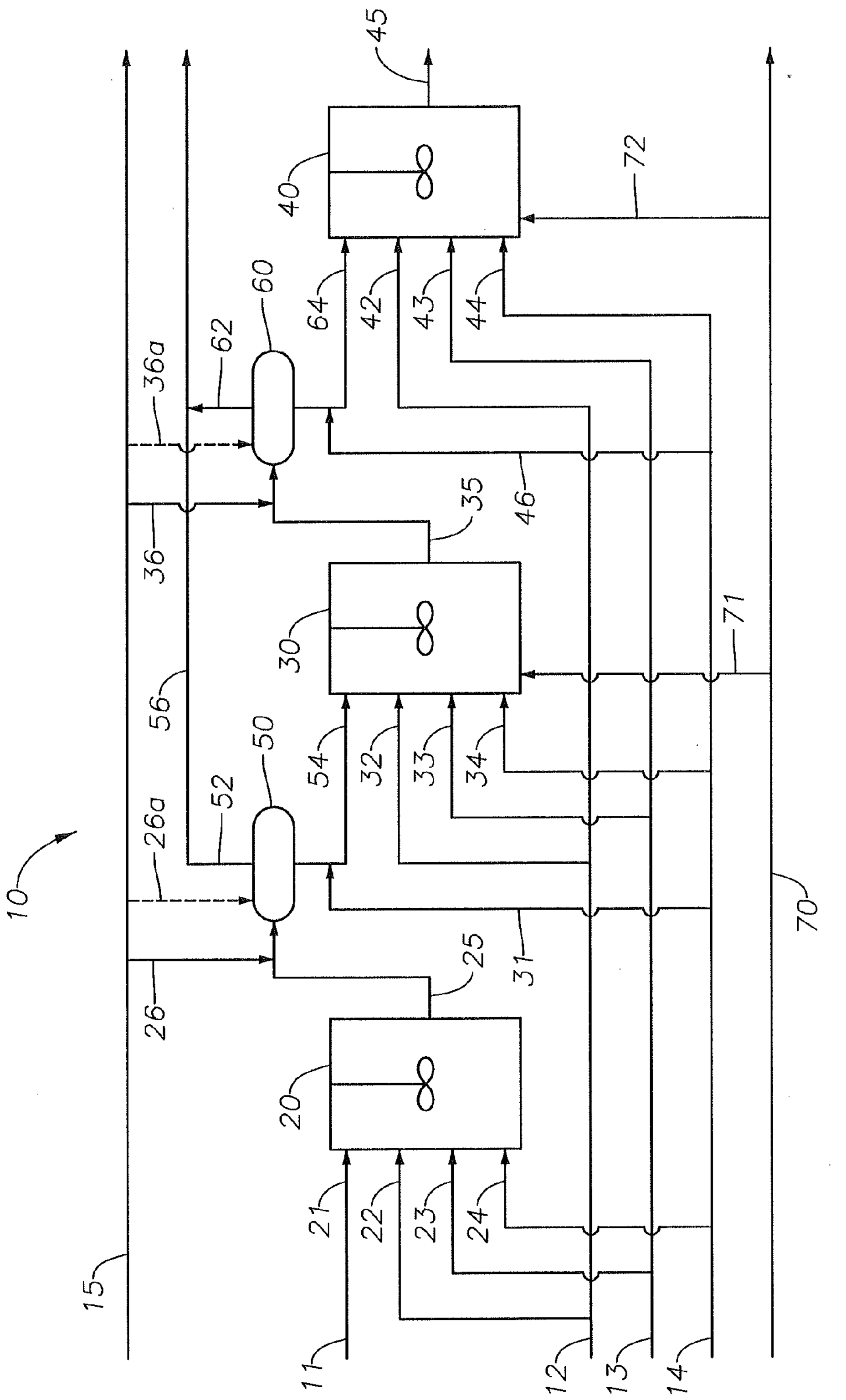
FIG. 1 illustrates a schematic representation of an embodiment of a device for the processing of a catalyst.

As used in the current specification, the expressions "epoxidation" and "oxidation" refer to the same reaction; the conversion of the carbon-carbon double bond of the olefinically unsaturated compound into an oxirane ring. The invention is hereafter discussed in greater detail. Chemical compounds having an oxirane ring are described herein as epoxide compounds.

The following description refers to Turn Over Number (TON) and Turn Over Frequency. As described herein the Turn Over Number refers to the number of moles of substrate that a mole of catalyst can convert before becoming deactivated. In particular, for the processes described herein Turn Over Number may refer to the number of moles of the olefinically unsaturated compound that a mole of the manganese complex can convert before becoming deactivated As described herein, Turn Over Frequency is the number of moles of the substrate being converted (turnover) by the catalyst in a period of time. As the Turn Over Frequency changes over time, the Turn Over Frequency can be represented by the Turn Over Number (TON) per unit of time, dTON/dt. In particular, Turn Over Number (TON) is calculated or measured by the temperature difference (dT) between the reaction mixture and the cooling medium as a measure of epoxidation rate, which translates into dTON/dt.

As used herein, "deactivation" is a process in which the complexes as described herein are reduced to the individual components with reduced or minimal complex structure retention, and have no or significantly reduced catalytic activity. Deactivation is observed when the catalytic activity, as measured by Turn Over Frequency (dTON/dt) is below 1000 TON/hour (TON/hr), such as from about 0 TON/hr to about 500 TON/hr. The UV-Vis data also illustrates reduces or minimal absorbance between wavelengths 250 to 350 nm (Table 7), which indicates the absence of a coordinate manganese in a oxidation state of $Mn^{3+}$ (III) or $Mn^{4+}$ (IV).

As used herein, "inactivation", is a process wherein the complexes described herein remain intact as complexes without deactivation in an aqueous medium. Inactivation of the catalytic activity, as measured by Turn Over Frequency is below 2000 TON/hr, such as from about 100 TON/hr to about 1000 TON/hr. The UV-Vis data illustrates absorbance between wavelengths 250 to 350 nm (Table 7) with a new and less intense visible absorption at 425 nm. This less intense absorption at 425 nm indicates that the manganese is in a 3+ oxidation state with the transformation of the active $Mn^{3+}$-catalyst to a catalytically inactive manganese complex for an epoxidation process.

As used herein, "reactivation", is a process wherein the inactive complexes described herein are chemically activated without loss of catalytic activity or with no significantly reduced catalytic activity, compared to the active complexes prior to inactivation, to perform as catalyst in a reaction mixture. Reactivation of the catalytic activity, as measured by Turn Over Frequency, is from 2000 TON/hr to about 20,000 TON/hr. The UV-Vis data also illustrates that the absorbance between wavelengths 250-350 nm, and the disappearance of visible absorbance at 425 nm (Table 7), indicates that the manganese is in a 3+ oxidation state and remains a catalytically active manganese complex for an epoxidation process.

Loss of UV-Vis absorbance at 350, 400, and 425 identifies the deactivated catalyst. Active and inactive catalysts display good absorbance at 350, 400 and 425 nm and are attributed to $Mn^{3+}$-species. Inactive $Mn^{3+}$-catalysts species are differentiated from the $Mn^{3+}$-active catalysts ($Mn^{III}$-active catalysts) from the increased absorbance at 425 nm as shown in Table 7 below.

In one embodiment, the invention provides for processing a composition having manganese complex (as a catalyst) by using the manganese complex in an epoxidation reaction, inactivating the manganese complex in the composition, and then reactivating the manganese complex for use in another epoxidation reaction.

It was surprisingly and unexpectedly discovered that the Turn Over Frequency of the manganese complex can be significantly reduced while the deactivation of the manganese complex does not occur or is significantly reduced when the pH of a reaction mixture or aqueous phase containing the manganese complexes is reduced to a pH of 2.5 or less. This surprising result was found since the ligands as described herein, with the exception of Cu2+ complexes of the ligands, are thermodynamically unstable at a pH level below 4 in the range of relevant catalyst concentrations. Additionally, the result was also surprising since it has been observed that at lower pH levels, complexes of such ligands have accelerated deactivation (de-complexation). Thus, the process described herein is based on the observation that a manganese complex may be catalytically inactivated while maintaining the manganese complex structure, and then reactivated for use as a catalyst at a later time.

The epoxidation process is carried out in a multiphasic system of an aqueous phase and at least one organic phase. The epoxidation process as described herein includes reacting an olefinically unsaturated compound with an oxidizer in the presence of a manganese complex as a catalyst, with an optional buffer component, in an aqueous medium at acidic conditions. The oxidation of the olefinically unsaturated compound is believed to take place in an aqueous phase, whereas the organic phase is believed to extract or strip produced 1,2-epoxide from the aqueous phase.

The pH of the epoxidation reaction is from greater than 2.5 to about 6, such as from about 2.8 to about 5.0, for example, from about 3 to about 3.6. The manganese complex of the epoxidation reaction may have a catalytic activity, as measured by Turn Over Frequency, from 2000 TON/hr to about 20,000 TON/hr, such as from about 2000 TON/hr to about 10,000 TON/hr.

The resulting system, or reaction mixture, may then be processed to allow the respective phases of the reaction mixture to settle into separable phases, such a separate aqueous phase and at least one separate organic phase. For example, the reaction mixture may be discharged from a reactor, with the discharged reaction mixture comprising both product and unreacted starting material, to a separator to settle into the aqueous phase containing the complexes described herein and the organic phase containing the epoxide product described herein. For example, the at least one organic phase may comprise two organic phases, with one organic phase comprising an epoxide product and a second organic phase comprising an organic reactant. It has been observed that the organic phase contains little or no water soluble by-products and catalyst.

The separated aqueous phase was observed to have the manganese complex in a catalytically active state. The pH of the separated aqueous phase is from greater than 2.5 to about 6, such as from about 2.8 to about 5.0, for example, from about 2.8 to about 3.8.

The manganese complex was further observed to accelerate deactivation when retained in the isolated aqueous phase.

Without being bound to any theory, it is believed that the presence of olefinically unsaturated compound allows the catalyst to remain active without accelerated deactivation, whereas it is believed that without the presence of olefinically unsaturated compound and/or due to the presence of the epoxide and/or oxidant without olefinically unsaturated compound present, the activity of the active catalyst reduces an accelerated rate.

It was surprisingly and unexpectedly discovered by the inventors, that the manganese complex may be retained in the aqueous phase without deactivation or with reduced deactivation of the manganese complex to the constituents by using a pH more acidic than the epoxidation process. This result was found to be surprising and unexpected since it is known in the art that lower pH levels lead to accelerated deactivation (de-complexation).

The manganese complex may be retained in the aqueous phase with no or minimal deactivation by reducing the pH of the aqueous phase to 2.5 or less, such as from about 1 to about 2. The pH of the aqueous phase may be reduced by the addition of a first pH adjusting agent, such as an acid, such as an inorganic acid, an organic acid, or combinations thereof. Suitable organic acids may include such as oxalic acid, acetic acid, formic acid, and combinations thereof, while suitable inorganic acids may include hydrochloric acid (HCl) sulphuric acid ($H_2SO_4$), nitric acid, and combinations thereof.

The inactivated manganese complex may be retained in the aqueous phase with no or minimal deactivation for a period of time from about 1 minutes to about 120 minutes, such as from about 5 minutes to about 60 minutes, for example, from about 5 minutes to 30 minutes. The inactivated manganese complex may have a catalytic activity, as measured by Turn Over Frequency, from about 0 TON/hr to less than 2000 TON/hr, such as from about 100 TON/hr to about 1000 TON/hr.

The manganese complex in the aqueous phase may then be reintroduced into or form a mixture containing the components for an epoxidation reaction with the aqueous phase having the pH adjusted to have the manganese complex in a catalytically active state. This may be achieved by increasing the pH of the aqueous medium to a pH from greater than 2.5 to about 6, such as from about 2.8 to about 3.8.

The pH may be adjusted by the addition of a second pH adjusting agent. The second pH adjusting agent may be an inorganic base, an organic base, or combinations thereof. Examples of suitable bases include compounds selected from the group of sodium hydroxide (NaOH), potassium hydroxide (KOH), calcium hydroxide ($Ca(OH)_2$), ammonium hydroxide ($NH_4OH$), aliphatic amines, potassium carbonate, sodium carbonate, potassium oxalate, sodium oxalate, and combinations thereof.

The reactivated manganese complex may have a catalytic activity, as measured by Turn Over Frequency, from 2000 TON/h to about 20,000 TON/h, such as from about 2000 TON/h to about 10,000 TON/h. In terms of water-soluble manganese complexes that may be used as oxidation catalyst, many suitable complexes are known. Note in this respect that what is described in this patent is actually the catalyst precursor. Indeed, in all open and patent literature typically a catalyst precursor is defined, as the active species during the system may be different and in fact even changing during the reaction that it catalyzes. For convenience sake, and as this is common in the literature, we refer to the complex as if the complex is the catalyst.

The manganese complex (catalyst) as described herein may be a mononuclear manganese complex, a binuclear manganese complex, or a polynuclear complex. Examples of such complexes include:

a mononuclear species of the general formula (I):

$$[LMnX_m]Y \quad (I);$$

a binuclear species of the general formula (II):

$$[LMn(\mu\text{-}X)_m MnL]Y_n \quad (II), \text{ or}$$

a polynuclear species of the general formula (I):

$$[L_n Mn_n(\mu\text{-}X)_m]Y_n \quad (III),$$

and a combination of the complexes, where Mn is manganese; L or each L is independently a polydentate ligand. Each X is independently a coordinating species and each μ-X is independently a bridging coordinating species, selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^-$, $HOO^-$, $H_2O$, $SH^-$, $CN^-$, $OCN^-$, $C_2O_4^{2-}$, and $SO_4^{2-}$ and combinations thereof, wherein R is a $C_1$-$C_{20}$ radical selected from the group consisting of alkyl, cycloalkyl, aryl, benzyl and combinations thereof. The manganese constituent may be in the oxidation states of +2 or +3 or +4. In the formulas, m may be from 1 to 3, for example 3, and n may be from 0 to 3, such as 1 or 2.

Y is a non-coordinating counter ion. The non-coordinating counter ion Y may provide for the charge neutrality of the complex and the value of n depends upon the charge of the cationic complex and anionic counter ion Y. Counter ion Y may for instance be an anion selected from the group consisting of $RO^-$, $Cl^-$, $Br^-$, $I^-$, $F^-$, $SO_4^{2-}$, $RCOO^-$, $PF_6^-$, tosylate, triflate ($CF_3SO_3^-$) and a combination thereof with R once again being a $C_1$ to $C_{20}$ radical selected from the group consisting of alkyl, cycloalkyl, aryl, benzyl and combination thereof. The type of anion is not very critical, although some anions are more preferred than others. In one embodiment, an ion of $CH_3COO^-$ or $PF_6^-$ may be used as the non-coordinating counter ion.

Polydentate ligands are multiple bond ligands capable of forming a coordination complex or metal complex. Suitable polydentate ligands include acyclic compounds containing at least 7 atoms in the backbone or cyclic compounds containing at least 9 atoms in the ring, each having the nitrogen atoms separated by at least two carbon atoms. A suitable class of ligands include 1,4,7-triazacyclononane ("Tacn") and substituted versions thereof. The substituted 1,4,7-triazacyclononane compound may be substituted with one or more organic groups having a $C_1$ to $C_{20}$ organic group selected from the group consisting of alkyl, cycloalkyl, aryl, and combination thereof. For example, 1,4,7-triazacyclononane, may be substituted by one or more methyl groups, to form N',N",N'"-trimethyl-1,4,7-triazacyclononane (TmTacn). Examples of suitable ligands include compounds selected from the group of N',N",N'"-trimethyl-1,4,7-triazacyclononane, 1,5,9-trimethyl-1,5,9-triazacyclododecane (1,5,9-$Me_3$TACD), 2-methyl-1,4,7-trimethyl-1,4,7-triazacyclononane (2-Me, 1,4,7-$Me_3$TACN), 2-methyl-1,4,7-triazacyclononane, and combinations thereof.

In one embodiment of the manganese complex, the manganese complexes are those of the formula $[Mn^{IV}_2(\mu\text{-}O)_3L_2](Y)_n$ (same as formula: $[LMn(\mu\text{-}O)_3MnL](Y)_n$), wherein n is 2, and L and Y have the meaning identified above, such as TmTacn as ligand, and $PF_6^-$ or acetate ($CH_3CO_2^-$, hereinafter OAc) as counterion. The catalyst system comprising a water soluble manganese complex is described above. One complex for the current invention comprises 1,4,7-trimethyl-1,4,7,-triazacyclononane ("TmTacn") as the ligand or ligands. This ligand is commercially available from Aldrich.

Additionally, the manganese complex may be formed in situ from the reaction of a free ligand and a source of manganese. The free ligand may be the ligand described herein. The manganese source may comprise any manganese salt suitable having manganese ions in the oxidation state of $Mn^{2+}$ (II). Suitable manganese salts may include manganese salts of organic acids, inorganic acids, or a combination thereof. Examples of suitable manganese salts include salts selected from the group consisting of manganese sulphate, manganese acetate, manganese nitrate, manganese chloride, manganese bromide, and combinations thereof. The manganese source may be provided as a solid or dissolved in an aqueous medium.

The water-solubility of the manganese complex formed is a function of all the aforementioned components and depending on the counter ion (anion) associated with the manganese complex. The manganese complex may have a water solubility of about 1 g/L or greater at 20° C., for example, from about 1 g/L to about 2 g/L at about 20° C.

The manganese complex may be used with the components for an epoxidation reaction to produce an epoxide product. The epoxidation process includes reacting an olefinically unsaturated compound with an oxidizer in the presence of a manganese complex as a catalyst, with an optional buffer component, in an aqueous medium at acidic conditions. Depending on the reactants and reaction type, the epoxidation process may be carried out at a temperature in the range from about −5° C. to about 60° C., such as from about 4° C. to about 40° C., for example, from about 5° C. to about 35° C. Moreover, the process may be carried out at reduced pressure or under increased pressure, such as from 0.1 bars to 20 bars, such as from 0.9 bars to 9 bars. For instance, a higher pressure may be used when propylene is epoxidized.

The epoxidation reaction may be performed in a homogenous biphasic system with the organic phase distributed in the aqueous phase. The organic phase may be distributed in the aqueous phase through a process such as agitation. The phase ratio by volume of the two phases may be a volume ratio of organic to aqueous phase from about 5:1 to 1:10, such as from about 1:1 to about 1:2.

It has been observed that improved epoxide product conversion rates may be achieved by the use of olefinically unsaturated compounds that have limited solubility in water, for example, allyl chloride and allyl acetate instead of conventionally used allyl alcohol. The multiphasic system may be created by adding the olefinically unsaturated compound with limited solubility to an aqueous phase in an amount greater than what dissolves in the aqueous phase. Suitable olefinically unsaturated compounds may have a maximum solubility of about 100 g/L (at 20° C.), such as from 0.01 g/L to 100 g/L at 20° C.

According to the invention, the olefinically unsaturated compound used is an epoxidizible olefin which may be functionalized. The olefinically unsaturated compound may be a liquid under process conditions, for example, allyl chloride or liquefied propylene, but also a gas, for example, gaseous propylene.

Examples of suitable olefinically unsaturated compounds include olefinically unsaturated compounds. In one embodiment, the olefinically unsaturated compound may have at least one unsaturated —C═C— bond, such as at least one unsaturated $—C{=}CH_2$ group. The olefinically unsaturated compound may comprise more than one unsaturated —C═C— bond. Moreover, the unsaturated —C═C— bond need not be a terminal group. Terminally olefinically unsaturated compounds may have one or more terminal $—C{=}CH_2$ bonds.

Suitable examples of olefinically unsaturated compound therefore include the following compounds:

$R—CH{=}CH_2$;

$R'—(CH{=}CH_2)_n$;

$X—CH{=}CH_2$;

$Y—(CH{=}CH_2)_2$;

wherein R is a radical of 1 or more carbon atoms optionally comprising 1 or more heteroatoms (such as oxygen, nitrogen or silicon); R' is a multivalent radical of 1 or more carbon atoms optionally comprising 1 or more heteroatoms wherein n corresponds with the valence of the multivalent radical; X is a halogen atom, and Y is an oxygen atom.

Of particular interest are olefinically unsaturated compounds selected from the compounds vinylhalides or allylhalides, such as vinylchloride or allylchloride; 1-alkenes, such as propene; a cycloalkene, including aromatic compounds; mono-, di- or polyallyl ethers of mono-, di- or polyols; mono-, di- or polyvinyl ethers of mono-, di- or polyols; mono-, di- or polyallyl esters of mono-, di- or polyacid; mono-, di- or polyvinyl esters of mono-, di- or polyacids; divinylethers or diallylethers; and combinations thereof.

In another embodiment of the present invention, the olefinically unsaturated compound is selected from allyl bromide, allyl chloride and allyl acetate. In another embodiment of the invention allyl chloride is used for the manufacture of epichlorohydrin, because of the commercial interest and ease of isolating the produced epichlorohydrin.

According to another embodiment of the present invention the olefinically unsaturated compound is propylene in order to produce propylene oxide, and the reaction may be carried out at temperatures in the range from −5° C. to 40° C. Propylene may be used in excess over the oxidant.

The epoxidation process may use oxidizers including oxygen-containing gases, inorganic peroxides, organic peroxides, peracids, permanganates, hydrogen peroxide precursors, and combinations thereof. The oxidizer may be provided at a concentration from about 0.05 wt. % to about 4 wt. %, such as from about 0.1 wt. % to about 3 wt. %, for example, from about 0.3 wt. % to about 2 wt. % of the composition. Suitable oxygen-containing gases include oxygen gas ($O_2$), atmospheric air, and combinations thereof. Suitable inorganic peroxides include, for example, hydrogen peroxide, sodium peroxide, urea hydroperoxide, and combinations thereof. Hydrogen peroxide precursors may include metals used to form hydrogen peroxide from hydrogen gas and oxygen gas.

For example, hydrogen peroxide may be used as the oxidizer. Hydrogen peroxide may be used in an aqueous solution at a concentration that may vary, from 15% to 98% (propellant grade), such as industrial grades varying from 20 to 80%, for example, from 30 to 70%. Hydrogen peroxide precursors may include metals used to form hydrogen peroxide from hydrogen gas and oxygen gas.

The epoxidation process is performed in an aqueous reaction medium (again, excluding any olefins and/or the corresponding oxides dissolved therein) that is essentially a 100% water phase.

In an alternative embodiment, the epoxidation processes may be performed with organic solvents in the aqueous phase. The current epoxidation process may be carried out in an aqueous reaction medium comprising 10 volume percent or less of co-solvents. The use of organic co-solvents, such as water-soluble alcohols, is believed to improve the solubility of the olefinically unsaturated compound. Suitable co-solvents include, for example, acetone, methanol, and other water-soluble alcohols. Examples of co-solvents include, for example, acetone, acetonitrile, methanol, tetra hydrofuran (THF), and combinations thereof. The amount of organic co-solvents may be reduced to a minimum and the reaction may be carried out in a reaction medium substantially composed of water. With the exclusion of the presence of the reactants and the epoxidation products, the aqueous reaction medium therefore suitably comprises at least 90% by volume of water (v %), such as at least 95 v %, for example, at least 99 v %, and in some embodiments, at least 99.9 v % of water. The aqueous reaction medium (again, excluding any olefins and/or the corresponding oxides dissolved therein) may be essentially a 100% water phase.

The manganese complex is used in catalytically effective amounts. Typically, the catalyst is used in a molar ratio of catalyst (Mn) to the oxidant of from 1:10 to 1:10,000,000, such as from 1:100 to 1:1,000,000, for example, from 1:1000 to 1:100,000. As a matter of convenience the amount of catalyst may also be expressed in terms of its concentration, when keeping in mind the volume of the aqueous medium. For instance, it may be used in a molar concentration (based on the Mn) of from about 0.001 to about 10 mmol/L, such as from about 0.01 to about 7 mmol/L and for example, from about 0.01 to about 2 mmol/L.

The molar ratio of olefinically unsaturated compound for the process of the current invention includes a molar ratio of olefinically unsaturated compound to oxidant that may be greater than 1:2. This ratio may be in the range of from about 1:1 to about 12:1. For example, the molar ratio may be about 1:1, about 1.2:1, about 2:1, or about 4:1, or in the range of 2:1 to 12:1. If too much oxidant is used, then the selectivity towards the 1,2-epoxide reduces due to the production of undesirable side-products. Another consequence of too much oxidant with respect to olefinically unsaturated compound is rapid catalyst deactivation. If not enough oxidant is used, then the turnover number is suboptimal. This is therefore significantly different from bleaching conditions described in the prior art, where excessive amounts of oxidant, i.e. hydrogen peroxide are used. To ensure optimal peroxide efficiency, the oxidant may be added to the aqueous phase at a rate about equal to the reaction rate of the catalytic oxidation.

The reaction (catalytic oxidation) of the olefinically unsaturated compound takes place in the aqueous phase. The aqueous phase may have a pH from about 1 to about 8, such as from about 2 to about 6, for example from about 3 to about 5.

The aqueous phase may further comprise a buffer system to stabilize the pH in a certain range. While the following component is referred to as a buffer component, the component may also function or be utilized as a co-catalyst, a bridging ion, and/or a co-ligand, as described herein for the respective components.

The pH may be stabilized in an acidic pH range of greater than 2.5 to less than 7, such as a pH level range between about 2.8 and about 6, for the epoxidation reaction. The pH is therefore (well) below that used when bleaching olefins with hydrogen peroxide as the oxidant, typically carried out at more alkaline conditions (for example, pH adjusted with $NaHCO_3$ to 9.0).

The buffer component may be used in a molar ratio to the manganese complex (catalyst) in the range from about 1:1 to about 17, 000:1, such as from about 1:10 to about 1:1000. Sufficient buffer component may be added to produce the second pH level. In some embodiments, the concentration of the buffer component in the aqueous phase may range from about 0.05 wt % to about 9 wt %, such as from about 0.1 wt % to about 1 wt %. According to still another embodiment of the invention, the buffer, if any, and oxidation catalyst are fed as a pre-mixed mixture.

The buffer component may comprise an acid or an acid with the corresponding acid salt, such as an organic acid-salt combination. Suitable acids include with aliphatic or aromatic organic acids, such as oxalic acid, acetic acid, citric acid and aromatic acids based on substituted benzoic acids, and combinations thereof; inorganic acids, such as hydrochloric acid, phosphoric acid, and combinations thereof; and combinations thereof. Suitable acid-salt combinations may be selected from the group of oxalic acid-oxalate salt, hydrochloric acid-sodium citrate, oxalic acid-oxalate salt, malonic acid-malonate salt, succinic acid-succinate, glutaric acid-glutrate, acetic acid-acetate salt, citric acid-citrate salt, disodium phosphate-monosodium phosphate, 4-chlorobutanoic acid-4-chlorobutanoate, ortho-chloro benzoic acid-salt, para-chloro benzoic acid-salt, ortho-flouoro benzoic acid-salt, para-fluoro benzoic acid-salt, and combinations thereof.

The aqueous phase may further comprise a phase transfer agent and/or a surfactant. The phase transfer agent and/or a surfactant may be used if an olefinically unsaturated compound has low solubility (for example, below 0.1 g/L water). Phase transfer agents that may be used in the process of the invention include quaternary alkyl ammonium salts. Surfactants that may be used in the process of the invention include non ionic surfactants such as Triton X100™ available from Union Carbide.

The reaction conditions for the catalytic oxidation may be quickly determined by a person skilled in the art. The reaction is exothermic, and cooling of the reaction mixture may be required. The reaction may be carried out at temperatures anywhere from −5° C. to 40° C., dependent upon such physical parameters as melting and boiling point of the used olefinically unsaturated compounds.

The epoxidation reaction is further performed under agitation or mixing conditions. For example, the epoxidation reaction may be performed in a reactor having a stirring disposed therein or in a loop reactor having a mixing component disposed before and/or within the loop reactor lines. The amount of agitation will vary based on the epoxidation process, and the invention contemplates that sufficient agitation is performed to provide for performing the process as described herein to provide results as described herein.

According to one embodiment of the invention, the epoxidation reaction is performed in a reactor having an inlet and an outlet. Reaction components as described herein are fed to the reactor by one or more inlets, and the resulting multiphasic system, or reaction mixture, is discharged though the outlet. The processing apparatus further includes a separating means, such as a separator, connected to the reactor outlet for separating the reaction mixture into the at least one organic phase and the aqueous phase as explained above. This separation means may comprise a straight forward liquid to liquid separator, such as a settling tank, since the product forms at least one separate organic phase and the organic phase separates from the aqueous phase when allowed to settle. Other devices such as hydrocyclones can also be used for separating the phases.

Prior to introduction into the separator or in the separator itself, the aqueous phase of the reaction mixture may be modified as described herein, to inactivate the manganese complexes of the catalyst system.

The aqueous phase may then be introduced into a second reactor or recycled into the original reactor. Inside the reactor or prior to introduction into the reactor, the aqueous phase of the reaction mixture may be modified as described herein, to reactivate the manganese complexes of the catalyst system.

The present invention is further explained by means of FIG. 1, which shows a schematic representation of an embodiment of a device for the manufacture of epoxide products and manganese complex processing.

It is noted here that the skilled person facing the task of constructing the device for carrying out the process according to the invention, will be aware that all process technological elements of the device are constructed and operated by using common general process technological knowledge.

In this embodiment, the apparatus 10 comprises one or more reactors. The reactors may be a variety of reactors adapted to perform epoxidation reactions, such as multiphase loop reactors as mentioned herein. Several reactor designs are suited to carry out the process according to the invention. The reactor may be a plug flow reactor (PFR). Due to the required high velocity for dispersing and the long residence times a PFR used in the present invention will be a very long PFR. The reactor may also be a continuous stirred tank reactor (CSTR). When using a CSTR, special care should be taken in dispersing the olefinically unsaturated compound into the aqueous phase. The reactor type will also include a cooling means for controlling the temperature of the catalytic oxidation process.

According to one embodiment of the invention, the catalytic oxidation may also be carried out in a loop reactor. In a loop reactor, the reaction mixture is circulated. When the circulation rate of the loop reactor is about 15 times the rate at which the aqueous components and the olefinically unsaturated compound is fed, such as the feed rate, the loop reactor may be described as a CSTR because of the high degree of back mixing. The advantage of using a loop reactor in the present process is that it allows for the well defined mixing behaviour of a pumped system combined with dispersing means in a compact reactor design.

The reactor according to the invention further comprises dispersing means for dispersing the organic olefinically unsaturated compound phase into the aqueous phase and cooling means for controlling the temperature of the catalytic oxidation, because of its exothermic nature.

The dispersing means may be a static mixer, since it is believed that a static mixer will provide maximum break up of organic droplets in the continuous aqueous phase. According to another embodiment of the invention fresh oxidant and olefin are fed to the aqueous phase in subdivided portions to the reactor through multiple inlet parts distributed over the reactor housing.

For illustrative purposes, the apparatus 10 is shown as having three reactors referenced as reactors 20, 30, and 40 of FIG. 1. Each reactor contains a series of component inlet lines, for example, as shown in FIG. 1, the series of component inlet lines fqr the reactor 20 include inlet lines 21, 22, 23, and 24, and an outlet line, such as outlet line 25 as shown in the FIG. 1. The respective inlet lines are coupled to respective component feed lines, such as feed lines 11, 12, 13, and 14. While not shown, each component feed line is coupled to a separate feeding tank to feed components into the respective reactors. For example, feed lines 11, 12, 13, and 14, may respectively be the manganese complex feed line 11, the olefinically unsaturated compound (such as allyl chloride) feed line 12, the oxidizer (such as hydrogen peroxide) feed line 13, and the buffer component feed line 14. The components are transported from the feeding tanks to the respective reactor through the respective lines by means of feeding pumps (also not shown).

The reaction mixture is discharged from the reactor 20 via the reactor outlet line 25 into a separating means 50. A first pH adjusting line 26 may be coupled to the reactor outlet line 25 between the respective reactor and the respective separating means. The first pH adjusting line 26 may be coupled to a source line 15 of an acid or a suitable acid/acid salt mixture or the buffer component feed line 14 (not shown), which source material may be used to reduce the pH of the fluid traveling through the reactor outlet line 25 prior to arriving at the separating means 50. Alternatively, the first pH adjusting line 26 is coupled to the separating mean 50 directly, shown as dotted line 26*a*.

In the separating means 50, such as a separator, the at least one organic phase and the aqueous phase are allowed to form distinct phases. The organic phase comprising an epoxide product, such as epichlorohydrin, is allowed to separate and then may be isolated from the separating means 50 through the product outlet 52, which is coupled to a product retrieval line 56.

At least part of the aqueous phase in the separating means 50 is reused. In one example the aqueous phase is delivered to a second reactor 30 via a conduit 54 connecting the separating means 50 and the second reactor 30. In an alternative embodiment, while not shown, the aqueous phase from the separator may be recycled back to the reactor 20. Additionally, and also not shown, additional aqueous phase containing the manganese complex, whether in an activated or inactivated state, such as from line 21 or another reactor's aqueous phase, may be mixed with the material in conduit 54 prior to addition to the reactor 30. A cycling pump (not shown) transports the aqueous phase through the cycling conduit.

A second pH adjusting line 31 is coupled to the conduit 54 between the respective separator means and the reactor. Alternatively, the second pH adjusting line 31 is coupled to the second reactor. The second pH adjusting line 31 contains a base as described herein that may be used to increase the pH of the aqueous phase prior to addition to the reactor. The second pH adjusting line 31 may also be a branch line from the main base feed line 14 as shown in FIG. 1.

The processes described herein may be continued using a second separator 60 and third reactor 40 for recycling the aqueous phase through another reaction process. The second separator 60 is fed from outlet line 35, and a pH adjusting line 36 is coupled to the outlet line 35, or alternatively to the reactor 40 by line 36*a*. An epoxide product exits the separator through the product outlet 62, which is coupled to a product retrieval line 56. The aqueous phase is delivered to the third reactor 40 via a conduit 64 connecting the separating means 60 and the third reactor 40. The third reactor 40 also includes product inlet lines 42, 43, and 44, and outlet line 45.

Additionally, an optional manganese complex replenishment line 70 may be coupled to subsequent reactors, such as lines 71 for reactor 30 and line 72 for reactor 40. The replenishment line 70 provides manganese complex, and optionally the buffer, to the reactor to provide that the reactor has sufficient amounts of manganese complex for catalyzing the epoxidation reaction. As the process described herein provides for the preservation or reduced deactivation of the manganese complex, the replenishment process may be required to replace the manganese complex that has already deactivated from the prior reaction.

The transfer means to any of the reactors may be achieved by the use of fluid conduit. For example, for recycling, the transfer means may be a pipe connecting an aqueous phase outlet of the separation means and a reactor inlet equipped with a pump to transport the aqueous phase into the originating reactor. For delivering the aqueous phase to a second reactor the transfer means may be a pipe connecting an aqueous phase outlet of the separation means and a second reactor's inlet equipped with a pump to transport the aqueous phase into the second reactor. It is noted here that the skilled person will be aware that the reactor according to the invention is equipped with standard process technological elements like for example, pumps, valves and control mechanisms.

In operation, the apparatus may be used as follows with the process described herein. While the following description illustrates the epoxidation of an allyl chloride, the invention contemplates that the process and any of the components described herein may be used in the apparatus described herein.

Initially, the olefinically unsaturated compound, such as allyl chloride, the oxidizer, such as hydrogen peroxide, and the manganese complex as described herein are charged with water to a reactor, such as reactor 20. A buffer component, such as a buffer of oxalic acid/oxalate salt may also be charged into the reactor. The components may be introduced simultaneously, periodically or sequentially into the reactor. The components are allowed to react and produce an epoxide component in a reaction mixture, such as epichlorohydrin from allyl chloride, as described herein. The reaction mixture may be multiphasic, such as at least one organic phase and one aqueous phase. The epoxide component will separate out into at least one of the organic phases. It is believed that is some embodiments, the organic precursor material, such as epichlorohydrin may form a second and separate organic phase from the epoxide containing organic phase.

The volumetric ratio of the organic phase to the aqueous phase, both inside the respective reactor, and the degree of contact between the phases are important parameters in the performance of the catalyst system. If the amount of organic phase is too high, the aqueous phase is no longer the continuous phase. In this case, there may be insufficient mixing of the ingredients. This means that the conversion rate of olefinically unsaturated compound is considerably lowered. On the other hand, if the aqueous phase inside the reactor is too high with respect to the amount of organic phase, the olefinically unsaturated compound concentration in the aqueous phase will be too low with respect to oxidant concentration. This may lead to the production of undesirable side products and catalyst deactivation. Therefore the volumetric ratio of aqueous phase to organic phase inside the reactor may be in the range of from 10:1 to 1:5, with emulsion formation as a maximum limit.

The above limitations can also be influenced by the degree of mixing. In practice this means that the organic phase needs to be well dispersed into the continuous aqueous phase, such as in the form of droplets, preferably as small as possible, for example, less than 3 mm. Upon dispersion of the organic phase into the aqueous phase, the reaction (catalytic oxidation) of the olefinically unsaturated compound and the oxidant in the presence of the catalyst may occur.

The reaction mixture is then transported to a separating means 50 via a reactor outlet line 25. A first pH adjusting agent from the first pH adjusting line 26 may be added to the reaction mixture in the reactor outlet line 25 or the separating means 50. The first pH adjusting agent may be an acid, such as an acid used in forming the buffer component described herein. Sufficient first pH adjusting agent may be added to adjust the pH to a level of less than 2.5, as described herein. Suitable organic acids may include such as oxalic acid, acetic acid, and combinations thereof, while suitable inorganic acids may include hydrochloric acid (HCl) sulphuric acid ($H_2SO_4$), and combinations thereof. The adjustment of the pH is believed to allow the manganese complex to be retained in the aqueous phase with no or minimal deactivation of the manganese complex.

In the separating means 50, the organic phase comprising an epoxide product, such as epichlorohydrin, may be isolated from the aqueous phase by removal of the organic phase through the product outlet 52.

The remaining aqueous phase in the separating means 50 may be reused by feeding at least a portion (part) of the separated aqueous phase to a next reactor or by recycling at least a portion of the separated aqueous phase to the prior reactor. The at least a portion of the aqueous phase may be cycled into the reaction mixture. This way, catalyst present in the cycled aqueous phase is not discharged and efficiently used again.

The aqueous phase may be cycled to the next reactor, such as reactor 30, by a cycling conduit 54 connecting the separating means 50 and the next reactor 30. A second pH adjusting line 36 for a second pH adjusting agent is coupled to the cycling conduit 54 between the respective separator means and the reactor. Alternatively, the second pH adjusting line 36 is coupled to the respective reactor. The second pH adjusting agent may be a base as described herein. Sufficient second pH adjusting agent may be added to adjust the pH to a level of 2.5 or greater. Suitable second pH adjusting agents include a base, for example, selected from the group consisting of group of sodium hydroxide (NaOH), potassium hydroxide (KOH), calcium hydroxide ($Ca(OH)_2$), ammonium hydroxide ($NH_4OH$), and combinations thereof. The adjustment of the pH is believed to allow the manganese complex to be retained in the aqueous phase with no or minimal deactivation of the manganese complex.

When the process is running, per unit time, certain volumes of aqueous starting materials, such as the oxidant, catalyst and, if needed, buffer, are supplied to the reaction mixture. These aqueous starting materials are indicated as the aqueous components. Simultaneously, per unit time, also a certain volume of separated aqueous phase is cycled into the reaction mixture. The mass ratio of the volume of aqueous components to the volume of recycled aqueous phase added to the reaction mixture at every instant is indicated as the water recycle ratio. In order to achieve the advantageous effects of recycling the catalyst, said water recycle ratio may be in the range of from about 10:1 to about 1:10, such as from about 2:1 to about 1:5 and for example, about 1:3.5. Also, turbulent conditions such as a high velocity of the aqueous phase will prevent agglomeration of the organic droplets dispersed in said medium.

The following experiments illustrate the processes for the manganese complex as described herein.

EXPERIMENTAL SET UP

The experiments were carried out in a jacketed glass batch reactor on 200 ml scale. The reaction mixture includes an organic phase containing the olefinically unsaturated compound and a water phase containing the manganese complex, the buffer component, and the oxidant, in which the oxidant is fed continuously. By stirring the organic mixture, the organic phase, is finely dispersed in the water phase where it reacts with hydrogen peroxide. The reactor is equipped with temperature control and pH control.

Experiment 1

A process was performed as described above. First, a reference experiment was performed in which the temperature was maintained at 5° C., and the pH controlled at 3.6. To 100 mL of water, 164 mg disodiumoxalate and 72 mg anhydrous oxalic acid was added. To this buffer solution, 0.203 mL of 3.5 wt % Dragon A350 (manganese complex) was added and stirred for 10 minutes. To the water phase, 100 mL allyl chloride was added. The allylchloride was dispersed in the water phase for 5 more minutes. Then, at t=0, hydrogen peroxide was dosed for 150 minutes according to the dosing schedule in Table 1 below. From t=0 to t=210, a 5 wt % oxalic acid solution in water was dosed at a flow rate of 6 mL/h. For pH control, 0.5 M NaOH was used.

TABLE 1

| Time (minutes) | 35 wt % $H_2O_2$ (mL/h) |
|---|---|
| 0-25 | 10 |
| 25-30 | 20 |
| 30-50 | 15 |
| 50-85 | 10 |
| 85-150 | 7 |
| 150-210 | 0 |

The above reference experiment was repeated three times, in which at t=60 the pH was changed to a secondary value, such as 1.5, 2.5 and 3.6 respectively, by dosing a 2 M HCl solution until the desired pH was reached. Then, $H_2O_2$ dosing and stirring were stopped for one hour to simulate the conditions in a settler with a residence time of one hour, thereby allowing the water and organic phases to settle.

After one hour, stirring was started; the pH adjusted back to 3.6 using the pH control and $H_2O_2$ dosing was started again according to the above dosing schedule. The result of an identical experiment as a reference reaction at a pH of 3.6 without settling was also performed. The reference reaction and the three reactions with settling were then plotted as Turn Over Number (TON) versus time as shown in FIG. 2

Figure 2:
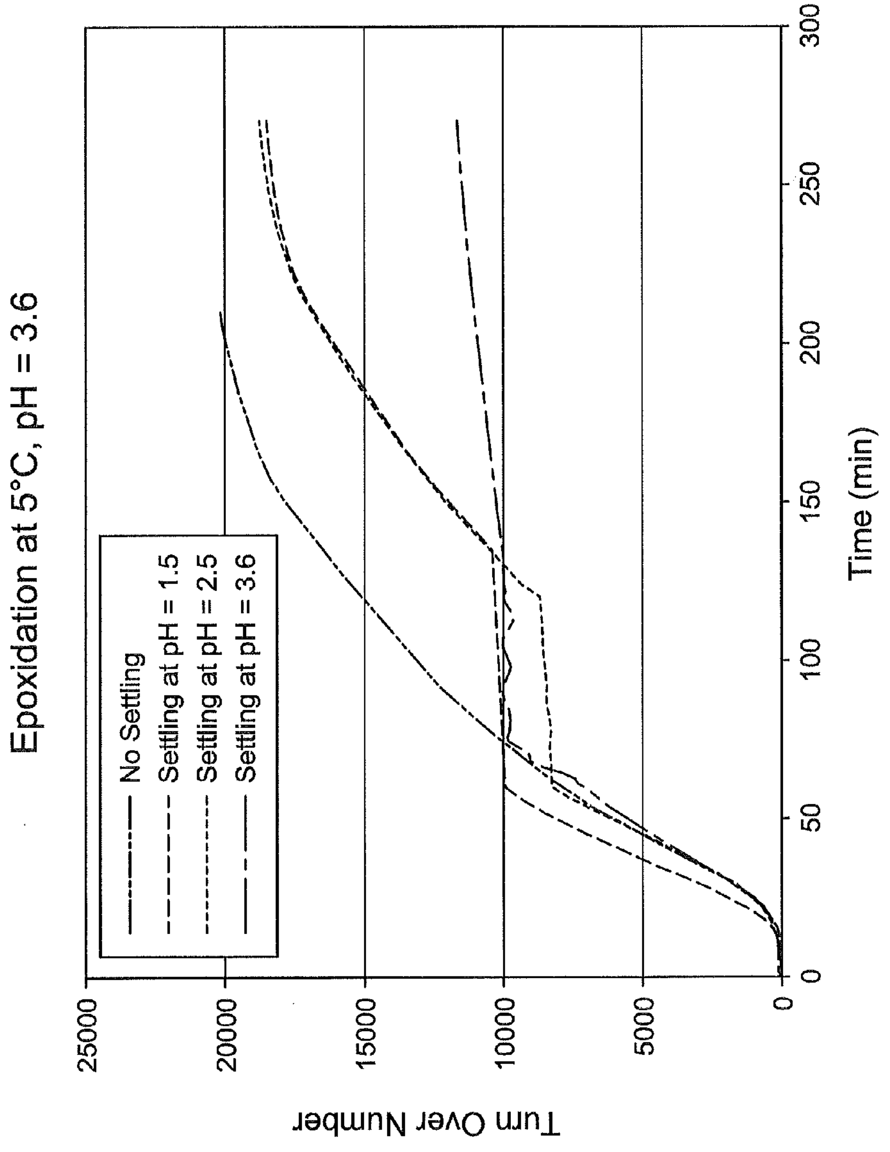
FIG. 2 illustrates a graph of a series of process results from one embodiment of the process described herein.

FIG. 2 illustrates that the reaction settling at pH=3.6 has a TON rate of 700 TON/hr, indicating that settling at a pH of 3.6 results in deactivation of the catalyst with minimal catalytic activity in a subsequent epoxidation reaction after settling. The experimental data for a pH of 1.5 and a pH of 2.5 indicate that settling at such pH levels has minimal effect on the catalyst activity compared to the reference without settling as shown in Table 2 below. The values in this table give the average TON/h after settling until t=210 compared to the reference between t=60 and t=150.

TABLE 2

| Reaction Type | Turn Over Frequency TON/hr |
|---|---|
| Reference | 6603 |
| After Settling at pH = 1.5 | 5144 |
| After Settling at pH = 2.5 | 5472 |
| After Settling at pH = 3.6 | 705 |

The final turn over numbers for the settling at pH values of pH 1.5 and 2.5 are only slightly lower than the reference, as shown in Table 3 below.

TABLE 3

| Reaction Type | Turn Over Frequency TON/hr |
|---|---|
| Reference | 20112 |
| After Settling at pH = 1.5 | 18479 |
| After Settling at pH = 2.5 | 18739 |
| After Settling at pH = 3.6 | 11641 |

Thus, as shown in FIG. 2 and Tables 2 and 3, the process described herein has resulted in the manganese complexes substantially maintaining the respective catalytic activity, with reduced or minimal deactivation of the manganese catalyst

Experiment 2

A process was performed as described above. First, a reference experiment was performed in which the temperature was maintained at 15° C., and the pH controlled at 3.6. To 100 mL of water, 164 mg disodiumoxalate and 72 mg anhydrous oxalic acid was added. To this buffer solution, 0.203 mL of 3.5 wt % $[Mn_2O_3(MeTACN)_2](OAc)_2$ (Dragon A350 manganese complex) was added and stirred for 10 minutes. To the water phase, 100 mL allyl chloride was added. The allylchloride was dispersed in the water phase for 5 more minutes. Then, at t=0, hydrogen peroxide was dosed for 180 minutes according to the dosing schedule in Table 4 below. From t=0 to t=210, a 5 wt % oxalic acid solution in water was dosed at a flow rate of 10 mL/h. For pH control, 0.5 M NaOH was used.

TABLE 4

| Time (minutes) | 35 wt % $H_2O_2$ (mL/h) |
|---|---|
| 0-6 | 10 |
| 6-15 | 18 |
| 15-40 | 13 |
| 40-80 | 9 |
| 80-150 | 6 |
| 150-180 | 5 |
| 180-210 | 0 |

The above reference experiment was repeated two times, in which at t=45 the pH was changed to a secondary value, such as 2.0 and 2.5 respectively, by dosing a 2 M HCl solution until the desired pH was reached. Then, $H_2O_2$ dosing and stirring were stopped for 30 minutes to simulate the conditions in a settler with a residence time of 30 minutes.

After 30 minutes, stirring was started, the pH adjusted back to 3.6 using the pH control and $H_2O_2$ dosing was started again according to the above dosing schedule. The reference reaction and the two reactions with settling were then plotted as Turn Over Number (TON) versus time as shown in FIG. 3.

Figure 3:
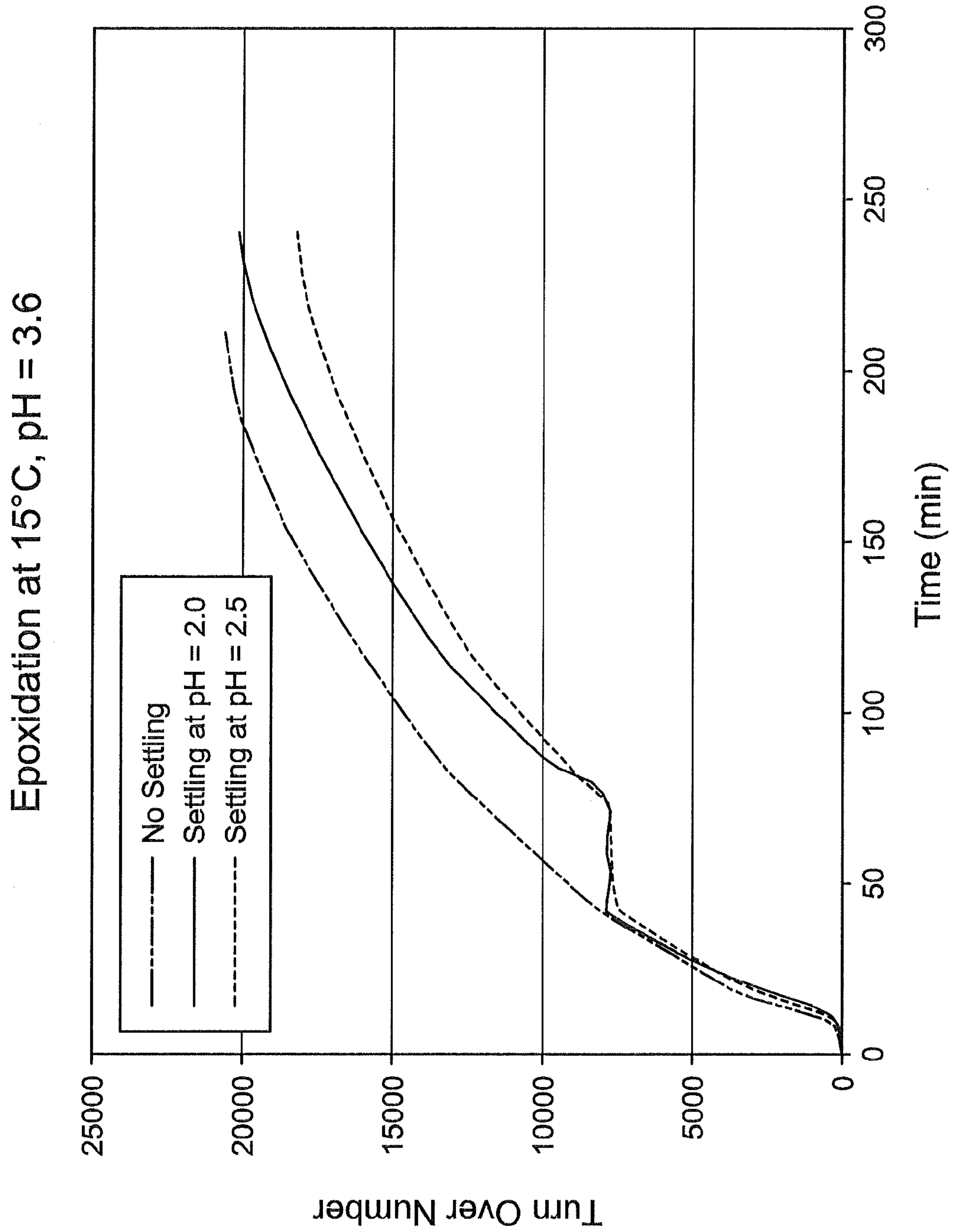
FIG. 3 illustrates a graph of a series of process results from another embodiment of the process described herein.

FIG. 3 illustrates that settling at pH of 2.0 gives better results in terms of TON/h and final TON, indicating less catalyst deactivation as compared to a pH of 2.5. The experimental data for settling at pH of 2.0 and 2.5 indicate that settling at such pH levels has a reduced or minimal effect on the catalyst activity compared to the reference without settling as shown in Table 5 below. The values in this table give the average TON/h after settling until t=210 compared to the reference between t=45 and t=180.

TABLE 5

| Reaction Type | Turn Over Frequency TON/hr |
|---|---|
| Reference | 5040 |
| After Settling at pH = 2.0 | 5054 |
| After Settling at pH = 2.5 | 4255 |

The final turn over number is only slightly lower than the reference, as shown in Table 6 below.

TABLE 6

| Reaction Type | Turn Over Frequency TON/hr |
|---|---|
| Reference | 20665 |
| After Settling at pH = 1.5 | 20195 |
| After Settling at pH = 2.5 | 18270 |

Manganese complexes at various pH levels were subjected to an UV-Vis spectra analysis during the manganese complex forming process. The UV-Vis analysis includes an in-line spectral analysis of the mixture during the process of the active catalyst preparation and with the application of various pH levels. The UV-Vis analysis is performed with an UV-V is spectrometer supplied by Avantes Company B.V. Halogen lamp is used as light source with the wavelengths range from 210 to 600 nm. Water was used as an internal reference to collect the UV-Vis spectra of the mixture at designated intervals of time during the catalyst preparation. An in-line probe is placed in the reactor in order to collect the spectra during the preparation of the catalyst and also to see the changes of the catalyst at various pH levels.

The UV-Vis spectra were used to determine the type of the catalyst species such as catalyst precursor, active catalyst, inactive catalyst (at low pH) and the deactivated catalyst with the measurement of Intensity/Absorbance in arbitrary unit versus wavelengths of manganese complex. The manganese complex absorbs wavelengths in the range of 250 nm to 350 nm, and the extent of the absorbance corresponds to the amount of manganese complex. The Mn-TMTACN catalysts of $Mn^{3+}$ and $Mn^{4+}$-TMTACN ($Mn^{IV}$-TMTACN) complexes display UV-Vis spectra with strong absorptions between 250 to 350 nm accompanied by weak absorptions 400 and 500 nm. Thus, the Intensity/Absorbance at around 350 nm correspond to the amount of manganese complex.

The UV-Vis spectral data of the aqueous solution was obtained in a model experiment by the changes in the pH in order to mimic the epoxidation reactions explained in Examples 2 and 3. The UV-Vis spectra of aqueous solution containing catalyst precursor $[Mn_2L_2O_3](OAc)_2$ at 0.24 mmol/L, oxalate buffer at 48 mmol/L and $H_2O_2$ at 11 mmol/L in water are measured at 5° C. from 200 to 600 nm.

The reaction was started at stage (i) with the stirring of catalyst precursor, oxalate and dilute $H_2O_2$ at 5° C., and this step was carried out for an hour. In the second step, stage (ii), the pH of the reaction mixture was reduced to 2.4 and stayed for 1 hour under stirring conditions. In the third step, stage (iii), the pH was increased again to 3.8 and continued the reaction for 2 hours. Measurements were performed at these three distinct stages and found different catalyst species. They are essentially catalyst precursor at pH of 3.8 at the start of stage (i), an active catalyst at 0.5 hours time period of stage (i), an inactive catalyst species at a pH of 2.4 in stage (ii), and the deactivated catalyst at the end of the stage (iii) at a pH of 3.8. Table 7 as follows illustrates the respective UV-Vis data for the activated, deactivated, and inactivated manganese complexes.

TABLE 7

| Wavelength (nm) | Precursor ($Mn^{4+}$) | Active catalyst ($Mn^{3+}$) | Inactive catalyst ($Mn^{3+}$) | Deactivated catalyst |
|---|---|---|---|---|
| 350 | 0.58 | 0.58 | 0.58 | 0.02 |
| 400 | 0.31 | 0.18 | 0.22 | 0.01 |
| 425 | 0.21 | 0.18 | 0.24 | 0 |
| 500 | 0.12 | 0.1 | 0.07 | 0 |

At the start of the stage (i), catalyst precursor was observed to have a manganese complex of $Mn^{4+}$ in the aqueous solution. An active catalyst species was formed at 0.5 hours time period in stage (i) at a pH of 3.8, which was observed to have a manganese complex of $Mn^{3+}$, and in the stage (ii) an inactive catalyst at a pH of 2.4 was formed which is also observed to contain manganese in the oxidation state +3. Oxalate and dilute $H_2O_2$ were helped to reduce the catalyst precursor ($Mn^{4+}$) to an active catalyst ($Mn^{3+}$) in the first step. When the pH was adjusted to a pH of 2.4, the active $Mn^{3+}$-catalyst was converted into an inactive catalyst species during period held at the lower pH. After one hour, the inactive catalyst species composition at pH 2.4 was adjusted to a pH of 3.8 and found that all the inactive catalyst is converted back into $Mn^{3+}$ active catalyst. The $Mn^{3+}$-active catalyst at pH 3.8 converted slowly into deactivated catalyst in a span of 2 hours.

All catalyst species at stages (i), (ii) and (iii) were observed to have near identical absorbencies of about 0.58 intensity (arbitrary units) at the wavelength of 350 nm. The similar absorbencies indicate that the amount of the manganese complexes was maintained and exhibit minimal if no deactivation during the pH adjustments. Additionally, the inactive catalyst species at stage (ii) was observed to maintain the same absorbencies from the initial pH adjustment through the one hour pH hold period. Such an indication corresponds to the stability of the amount of manganese complex in the pH 2.4 adjusted composition over a period of time with minimal or no indication of deactivation. Also, a quantitative conversion of inactive catalyst species in stage (iii) back to the active catalyst was observed based on the same absorbencies from the pH adjustment through the one hour pH hold period. At the end of the step (iii) the catalyst is converted into deactivated catalyst in 2 hour time period.

Catalyst precursor ($Mn^{+4}$) displayed two weak visible absorptions at around 400 and 500 nm along with an intense charge transfer band (CT band) from 250-350 nm. Conversion of catalyst precursor to active catalyst ($Mn^{3+}$) in stage (i) is evident from the decrease of the intensity of two weak visible absorptions. When the pH was reduced to 2.4, the active catalyst was converted into a $Mn^{3+}$-inactive catalyst. Presence of inactive species is evident from the appearance of visible absorption at 425 nm with the maintenance of same concentration based on the absorption at 350 nm. Temporary inactive species at stage (ii) at a pH of 2.4 are quantitatively reversible back to the active catalyst species when the pH is raised to above 3.8.

While the present invention has been described and illustrated by reference to particular embodiments, those of ordinary skill in the art will appreciate that the invention lends itself to variations not necessarily illustrated herein.

What is claimed is:

1. A process for processing a multiphasic system comprising:

reacting an olefinically unsaturated compound with an oxidant in the presence of a buffer component and a water-soluble manganese complex disposed in an aqueous phase having a first pH level in a first multiphasic system;

adjusting the pH of the aqueous phase to a second pH level less than the first pH level;

isolating at least a portion of the aqueous phase from the first multiphasic system and retaining the water-soluble manganese complex in the aqueous phase;

adjusting the pH of the at least a portion of the aqueous phase to a third pH level greater than the second pH level; and introducing the at least a portion of the aqueous phase into a second multiphasic system, wherein adjusting the pH of the aqueous phase to the second pH level comprises inactivating the water-soluble manganese complex and wherein adjusting the pH of the at least a portion of the aqueous phase to the third pH level comprises reactivating the water-soluble manganese complex.

2. The process according to claim 1, wherein reacting the olefinically unsaturated compound with the oxidant in the first multiphasic system comprises:

adding the oxidant and the water-soluble manganese complex as aqueous components to the first multiphasic system; and dispersing the olefinically unsaturated compound into the aqueous phase.

3. The process according to claim 1, wherein the first pH level is from greater than 2.5 to 6.

4. The process according to claim 1, wherein the second pH level is 2.5 or less.

5. The process according to claim 1, wherein the adjusting the pH of the aqueous phase to the second pH level comprises adding an acid selected from the group oxalic acid, acetic acid, formic acid, nitric acid, hydrochloric acid, sulphuric acid, and combinations thereof.

6. The process according to claim 1, wherein the third pH level is from greater than 2.5 to 6.

7. The process according to claim 1, wherein adjusting the pH of the aqueous phase to the third pH level comprises adding a base selected from the group consisting of sodium hydroxide, potassium hydroxide, calcium hydroxide, ammonium hydroxide, potassium carbonate, sodium carbonate, potassium oxalate, sodium oxalate, and combinations thereof.

8. The process of claim 1, wherein the first pH level and the third pH level are the same pH level.

9. The process of claim 1, further comprising:

reacting a second olefinically unsaturated compound with a second oxidant in the presence of a second buffer component and the water-soluble manganese complex in an aqueous phase having the third pH level in the second multiphasic system.

10. The process of claim 1, wherein the water-soluble manganese complex has a first Turn Over Number rate from 2000 TON/hr to about 20,000 TON/hr at the first pH level, a second Turn Over Number rate from about 0 TON/hr to less than 2000 TON/hr at the second pH level, and a third Turn Over Number rate from 2000 TON/hr at the third pH level.

11. The process of claim 1, wherein a time period between adjusting the pH of the aqueous phase to a second pH level and adjusting the pH of the aqueous phase to a third pH level is from about 1 minute to about 120 minutes.

12. The process of claim 1, wherein the manganese complex comprises:

a mononuclear species of the formula (I):

$$[LMnX_m]Y \quad (I),$$

a binuclear species of the formula (II):

$$[LMn(\mu\text{-}X)_m MnL]Y_n \quad (II), \text{ or}$$

a polynuclear species of the formula (III):

$$[L_n Mn_n(\mu\text{-}X)_m]Y_n \quad (III), \text{ and}$$

wherein Mn is manganese; L or each L is independently a polydentate ligand, each X is independently a coordinating species and each μ-X is independently a bridging coordinating species, wherein Y is a non-coordinating counter ion and m is from 1 to 4 and n is from 1 to 2.

13. The process of claim 12, wherein each coordinating species and each bridging coordinating species is selected from the group consisting of $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, $C_2O_4^{2-}$, and $SO_4^{2-}$and combinations thereof, wherein R is a $C_1$-$C_{20}$ radical selected from the group consisting of alkyl, cycloalkyl, aryl, benzyl and combinations thereof, and Y is a non-coordinating counter ion.

14. The process of claim 1, further comprising adding a second manganese complex to the second multi-phasic system.

15. The process of claim 13, wherein Y is an anion selected from the group consisting of $RO^-$, $Cl^-$, $Br^-$, $I^-$, $F^-$, $SO_4^{2-}$, $RCOO^-$, $PF_6^-$, tosylate, triflate ($CF_3SO_3^-$) and a combination thereof with R once again being a $C_1$ to $C_{20}$ radical selected from the group consisting of alkyl, cycloalkyl, aryl, benzyl and combination thereof.

* * * * *